United States Patent
Jackson

(10) Patent No.: US 12,156,999 B2
(45) Date of Patent: Dec. 3, 2024

(54) VENTRICULAR GEOMETRIC AND HEMODYNAMIC CONTROL BY HEART RATE MODULATION IN LVAD THERAPY

(71) Applicant: Medtronic, Inc., Minneapolis, MN (US)

(72) Inventor: Troy Jackson, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 924 days.

(21) Appl. No.: 16/952,694

(22) Filed: Nov. 19, 2020

(65) Prior Publication Data

US 2021/0228790 A1    Jul. 29, 2021

Related U.S. Application Data

(60) Provisional application No. 62/967,085, filed on Jan. 29, 2020.

(51) Int. Cl.
*A61M 60/523* (2021.01)
*A61M 60/178* (2021.01)
*A61M 60/432* (2021.01)

(52) U.S. Cl.
CPC ........ *A61M 60/523* (2021.01); *A61M 60/178* (2021.01); *A61M 60/432* (2021.01); *A61M 2205/3334* (2013.01); *A61M 2205/35* (2013.01)

(58) Field of Classification Search
CPC ........ A61M 1/10; A61M 1/12; A61M 1/1063; A61M 1/1086; A61M 60/523
See application file for complete search history.

(56) References Cited

U.S. PATENT DOCUMENTS

| | | |
|---|---|---|
| 6,688,861 B2 | 2/2004 | Wampler |
| 7,314,449 B2 | 1/2008 | Pfeiffer et al. |
| 7,575,423 B2 | 8/2009 | Wampler |
| 7,976,271 B2 | 7/2011 | LaRose et al. |
| 8,419,609 B2 | 4/2013 | Shambaugh, Jr. et al. |
| 8,744,601 B2 | 6/2014 | Spotnitz et al. |
| 8,864,644 B2 | 10/2014 | Yomtov |

(Continued)

FOREIGN PATENT DOCUMENTS

| | | |
|---|---|---|
| WO | 2011123789 A1 | 10/2011 |
| WO | 2016137743 A1 | 9/2016 |

OTHER PUBLICATIONS

International Search Report and Written Opinion dated Apr. 1, 2021, for corresponding International Application No. PCT/US2020/066925; International Filing Date: Dec. 21, 2020 consisting of 9-pages.

(Continued)

*Primary Examiner* — Matthew W Schall
(74) *Attorney, Agent, or Firm* — Shumaker & Sieffert, P.A.

(57) ABSTRACT

A method of operating an implantable blood pump and a pacing device, the method includes determining an end diastolic volume (EDV) and ejection fraction of one from the group consisting of the right ventricle and the left ventricle at a predetermined pump set speed. An average flow rate based on the predetermined pump set speed is determined. A target heart rate based at least in part on the determined EDV, ejection fraction, and average flow rate is determined. A lower rate for the pacing device is determined, the pacing device being in electrical communication with a chamber of the heart. The chamber of the heart is paced when a measured heart rate drops below the lower rate.

19 Claims, 5 Drawing Sheets

(56) References Cited

U.S. PATENT DOCUMENTS

| | | |
|---|---|---|
| 9,387,284 B2 | 7/2016 | Heilman et al. |
| 2006/0293714 A1 | 12/2006 | Salo et al. |
| 2007/0185369 A1 | 8/2007 | Mirhoesini et al. |
| 2019/0126014 A1 | 5/2019 | Kapur et al. |
| 2019/0275225 A1 | 9/2019 | Brown |
| 2019/0336767 A1 | 11/2019 | Klepfer et al. |

OTHER PUBLICATIONS

Ellen Ostenfeld and Frank A Flaschskampf, Assessment of right ventricular vols. and ejection fraction by echocardiography: from geometric approximations to realistic shapes, Published by Bioscientifica Ltd, ID: 14-0077; Mar. 2015 DOI: 10.1530/ERP-14-0077.

VENTRICULAR GEOMETRIC AND HEMODYNAMIC CONTROL BY HEART RATE MODULATION IN LVAD THERAPY

CROSS-REFERENCE TO RELATED APPLICATION

This application claims the benefit of U.S. Application Ser. No. 62/967,085, filed Jan. 29, 2020.

FIELD

The present technology is generally related to a method of operating an implantable blood pump and a pacing device.

BACKGROUND

About 80% of patients with implantable blood pumps, for example, a left ventricular assist device (LVAD) have or will have a cardiac rhythm management device, for example a pacing device, also implanted. Over the long term, about 15-25% of patients with an LVAD experience right ventricle failure. Currently, VADs and pacing devices do not communicate with each other during use, or use information from each other when being programmed.

SUMMARY

The techniques of this disclosure generally relate to a method of operating an implantable blood pump and a pacing device.

In one aspect, the present disclosure provides a method of operating an implantable blood pump and a pacing device, the method includes determining an end diastolic volume (EDV) and ejection fraction of one from the group consisting of the right ventricle and the left ventricle at a predetermined pump set speed. An average flow rate based on the predetermined pump set speed is determined. A target heart rate based at least in part on the determined EDV, ejection fraction, and average flow rate is determined. A lower rate for the pacing device is determined, the pacing device being in electrical communication with a chamber of the heart. The chamber of the heart is paced when a measured heart rate drops below the lower rate.

In another aspect of this embodiment, the EDV and ejection fraction are determined using echocardiography.

In another aspect of this embodiment, the method further includes measuring a flow rate from the implantable blood pump and updating the target heart rate based at least in part on the measured flow rate.

In another aspect of this embodiment, the implantable blood pump is a left ventricular assist device (LVAD), and wherein the EDV and ejection fraction is determined from the right ventricle.

In another aspect of this embodiment, the chamber of the heart is the right ventricle.

In another aspect of this embodiment, the implantable blood pump is a right ventricular assist device (RVAD), and wherein the EDV and ejection fraction is determined from the left ventricle.

In another aspect of this embodiment, the chamber of the heart is the left ventricle.

In another aspect of this embodiment, the method further includes pacing the left ventricle when a measured heart rate drops below the lower rate.

In another embodiment, a method of operating an implantable blood pump and a pacing device in communication with the implantable blood pump includes measuring an average flow rate of blood exiting the implantable blood pump. The measured average flow rate is communicated to the pacing device. An end diastolic volume (EDV) and ejection fraction of one from the group consisting of the right ventricle and the left ventricle is determined. One of a target heart rate and a lower rate for the pacing device is determined based at least in part on the determined EDV and ejection fraction at the measured average flow rate, the pacing device being in electrical communication with a chamber of the heart.

In another aspect of this embodiment, the EDV and ejection fraction are determined using echocardiography.

In another aspect of this embodiment, the method further includes updating one from the group consisting of the lower rate for the pacing device and the target heart rate based at least in part on the measured flow rate.

In another aspect of this embodiment, the implantable blood pump is a left ventricular assist device (LVAD), and wherein the EDV and ejection fraction is determined from the right ventricle.

In another aspect of this embodiment, the chamber of the heart is the right ventricle.

In another aspect of this embodiment, the implantable blood pump is a right ventricular assist device (RVAD), and wherein the EDV and ejection fraction is determined from the left ventricle.

In another aspect of this embodiment, the chamber of the heart is the left ventricle.

In another aspect of this embodiment, the method further includes pacing one of the right ventricle and the left ventricle when a measured heart rate drops below the lower rate.

In another embodiment, a cardiac rhythm and blood flow management system includes an implantable blood pump and a pacing device in communication with the implantable blood pump, the pacing device having processing circuitry configured to: determine a lower rate for pacing a chamber of the heart based at least in part on a measured flow rate calculated from the implantable blood pump and received by the pacing device.

In another aspect of this embodiment, the pacing device is in electrical communication with the right ventricle.

In another aspect of this embodiment, the implantable blood pump is a left ventricular assist device.

In another aspect of this embodiment, the pacing device is configured to pace the right ventricle when a measured heart rate drops below the lower rate.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
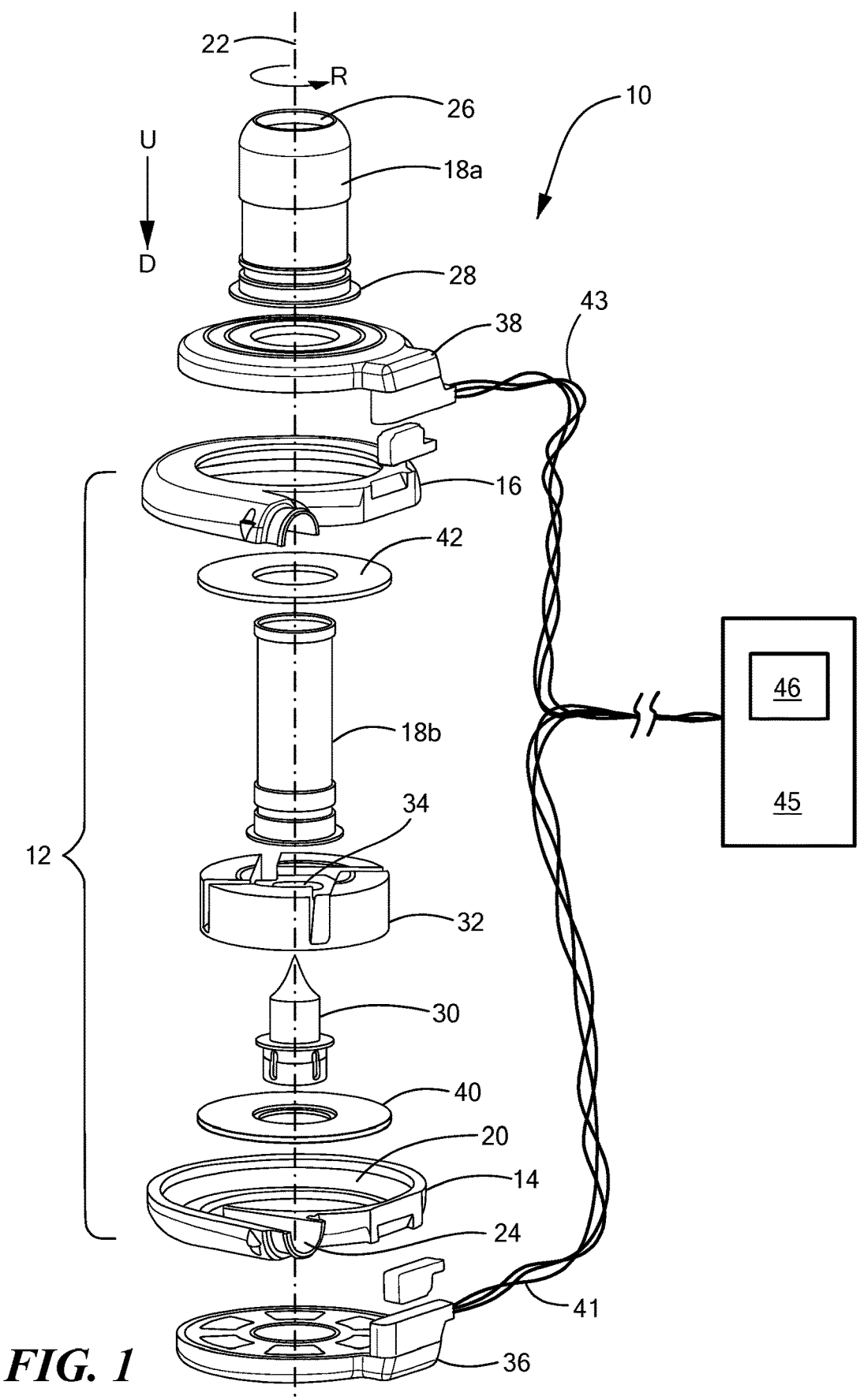
FIG. 1 is a schematic of an implanted blood pump and pacing device constructed in accordance with the principles of the present application.

Referring now to the drawings in which like reference designators refer to like elements there is shown in FIG. 1 an exemplary sensorless blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

The inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to first portion 14 along axis 22. A generally disc shaped ferromagnetic rotor 32 with a central hole 34 is mounted within chamber 20 for rotation about the axis 22. Rotor 32 includes a permanent magnet and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 are provided on the first stator 36 and the second stator 38 respectively for connecting the coils to a source of power such as a controller 45 having processing circuitry 46, which may be implanted or external to the patient. The controller 45 is arranged to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with elements of the first portion 14 and the second portion 16 during operation, as discussed in more detail below. The general arrangement of the components described above may be similar to the blood pump 10 used in the MCSD sold under the designation HVAD by Heart-Ware, Inc., assignee of the present application. The arrangement of components such as the magnets, electromagnetic coils, and hydrodynamic bearings used in such a pump and variants of the same general design are described in U.S. Pat.

Nos. 6,688,861; 7,575,423; 7,976,271; and 8,419,609, the disclosures of which are hereby incorporated by reference herein.

Figure 2:
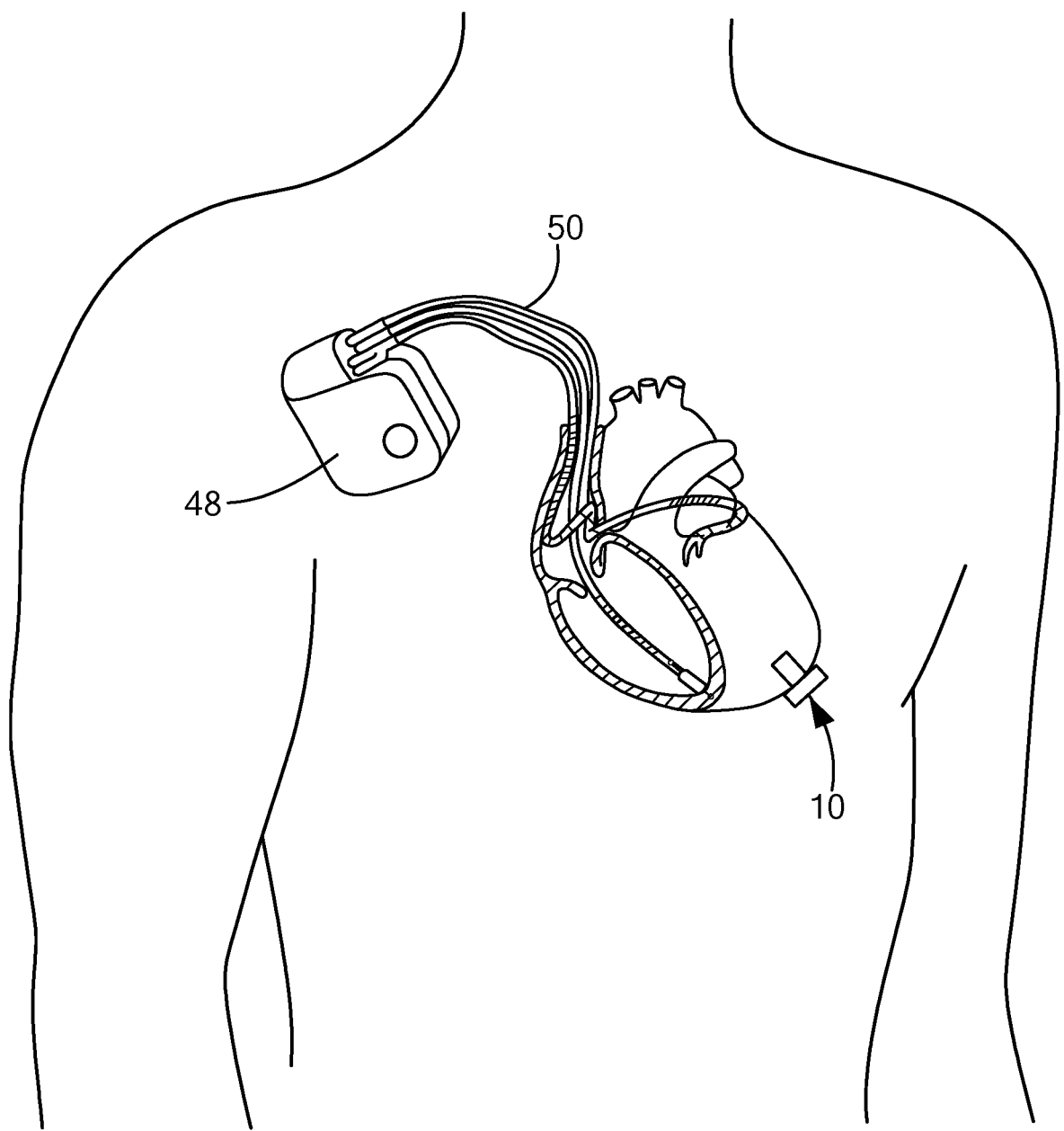
FIG. 2 is a schematic of an exemplary pacing device and the blood pump of FIG. 1 implanted within a patient.

Referring now to FIG. 2, a pacing device 48 may also be implanted within a human or animal patient. The pacing device 48 may be a pacemaker or any cardiac rhythm management device, such as an implantable cardioverter defibrillator configured to deliver electrical pulses to heart. The pacing device 48 may include one or more electrical leads 50 coupled to one or both of the left ventricle and the right ventricle, respectively. In one configuration, the pacing device 48 is programmable remotely. The pacing device 48 may further communicate with blood pump 10 wirelessly or through a wired connection. In the configuration shown in FIG. 2, the electrical leads are placed in the right ventricle and right atrium, but may be placed within or across any chamber(s) of the heart.

Figure 3:
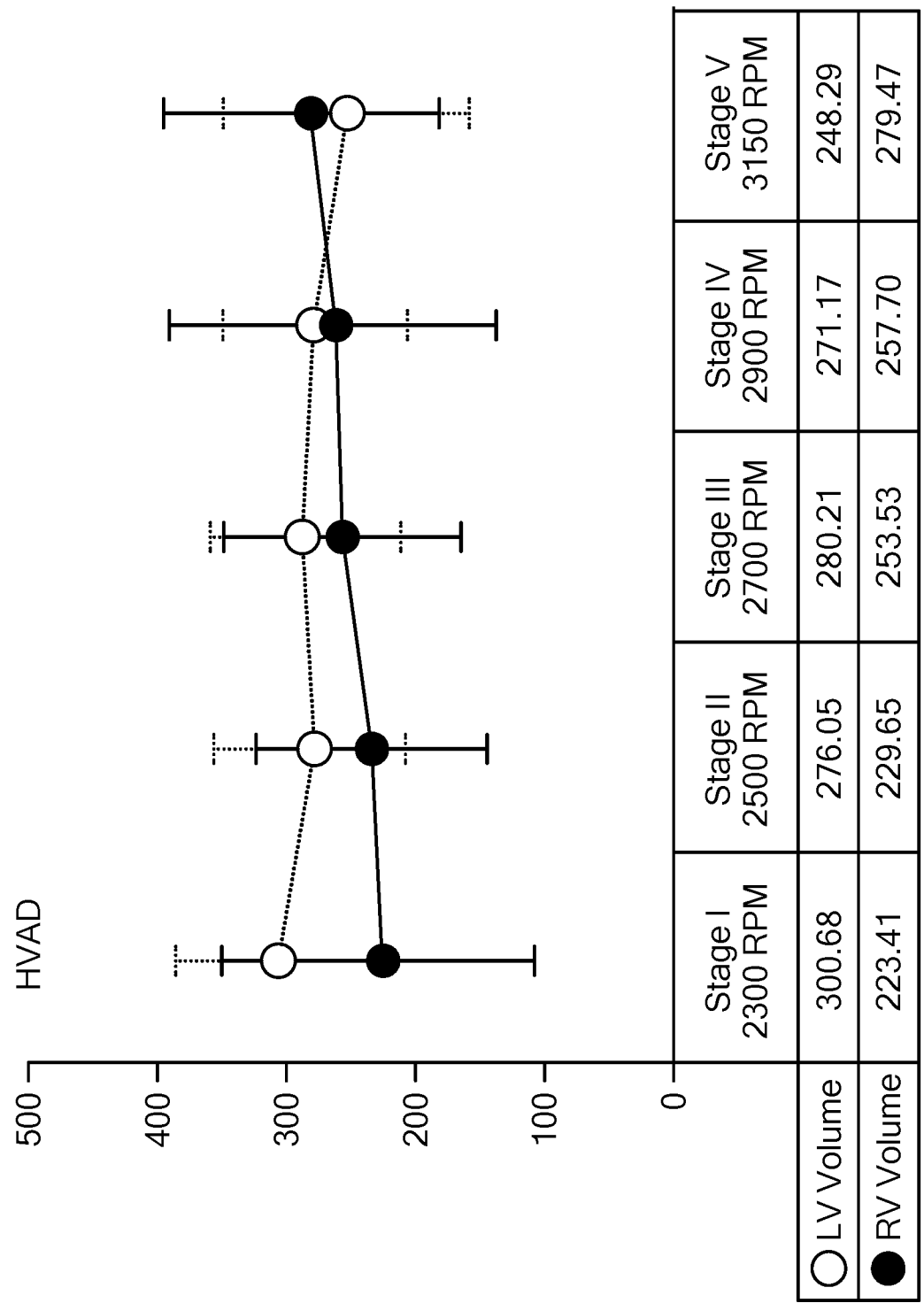
FIG. 3 is a graph showing the relationship between pump speed and ventricular volume
Figure 4:
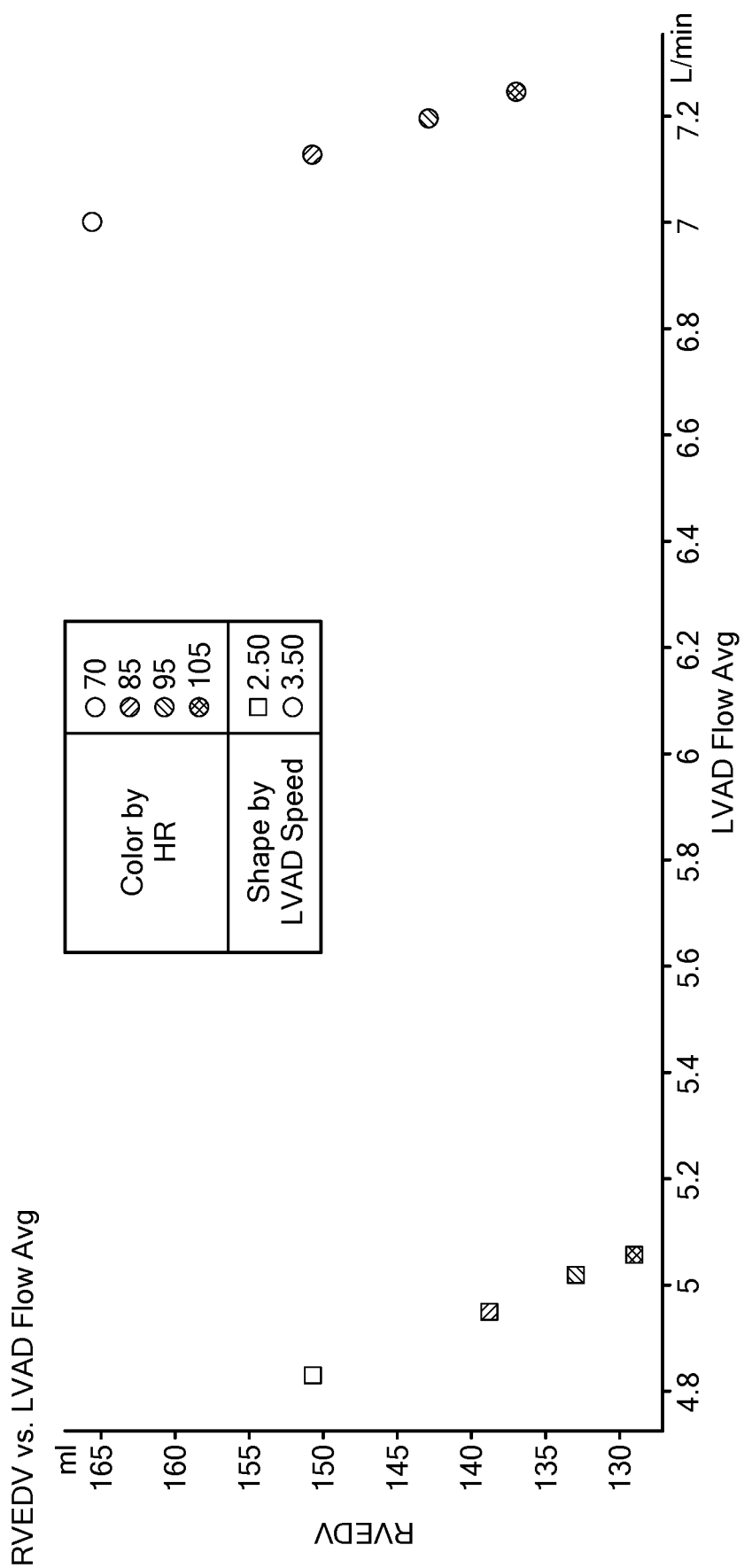
FIG. 4 is a graph showing the relationship between pump speed, RVEDV and flow rate.

Referring now to FIGS. 3-4, in a patient with a LVAD, a patient's heart rate is a function the flow from the blood pump, the right ventricular end diastolic volume (RVEDV) and the right ventricle ejection fraction (RVEF). In other words, the speed of the LVAD affects the right ventricle and left ventricle end-diastolic volumes. As shown in FIG. 3, as the speed of the LVAD increases left ventricle volume decreases while right ventricle volume increases. Moreover, as shown in FIG. 4, as the patient's heart rate (HR) increases, the RVEDV decreases. This relationship is governed by the equation:

$$\text{Flow (L/Min)} = \text{target HR (bpm)} * \text{RVEF (\%)} * \text{RVEDV (L)}$$

Thus, a target heart rate (HR) is related to LVAD flow, which is related to LVAD speed, the RVEF and the RVEDV in a patient with a LVAD. Similar, a patient with a right ventricular assist device (RVAD), a target heart rate (HR) is related to RVAD flow, which is related to RVAD speed, the LVEF and the LVEDV.

Figure 5:
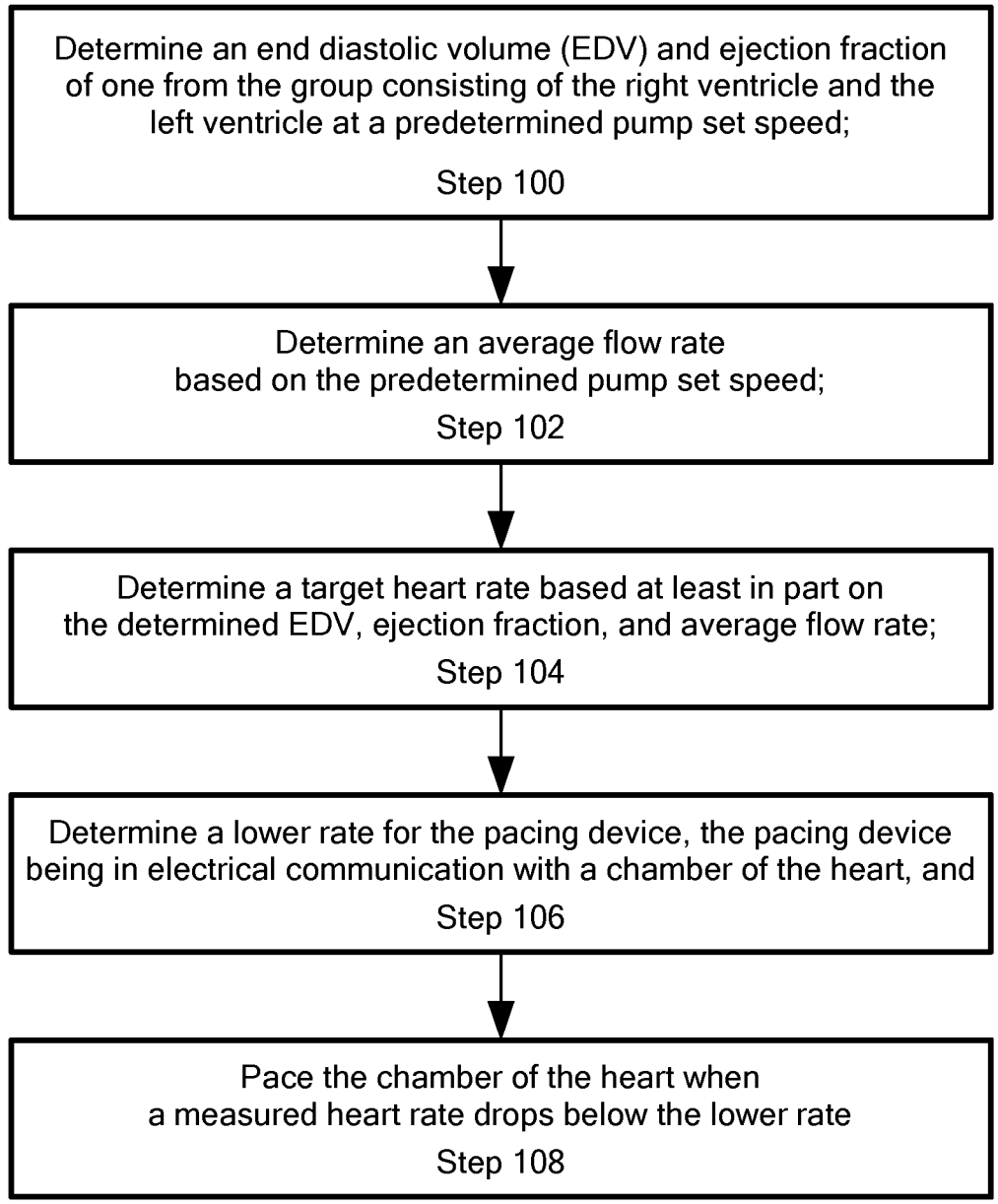
FIG. 5 is a flow chart showing a method of operating an implantable blood pump and pacing device.

Referring now to FIG. 5, a method of operating the implantable blood pump 10 and the pacing device 48 includes determining an end diastolic volume (EDV) and ejection fraction (EF) of one from the group consisting of the right ventricle and the left ventricle at a predetermined pump set speed (Step 100). In particular, depending on whether the patient has an RVAD or LVAD the opposite ventricle may be imaged using echocardiography to determine end diastolic volume and ejection fraction for a given pump set speed. An average flow rate based on the predetermined pump set speed may further be determined (Step 102). For example, flow rate may be correlated to the revolutions per minute of the pump set speed. A target heart rate based at least in part on the determined EDV, EF, and average flow rate may then be determined (Step 104). A lower rate for the pacing device 48 may then be determined (Step 106). In particular, the lower rate refers to the heart rate at which the pacing device 48 may pace the heart to increase the heart rate to a faster rate, for example, below 60 bpm. In such a configuration, the pacing device 48 may be in electrical communication with a chamber of the heart, for example, one from the group consisting of the right ventricle, left ventricle, right atrium, or left atrium to measure the patient's heart rate and to pace the heart. If the target heart rate drops below the lower rate, the pacing device 48 may apply an electrical pulse to one of the chambers of the heart to pace the heart (Step 108).

The target heart rate may be programmed remotely into the pacing device 48 through wireless communication and may be updated depending on the average flow rate. For example, the pacing device 48 may in wireless communication with the blood pump, for example, by Bluetooth or other forms of wireless communication and may communication the processing circuitry on board the pacing device 48 to indicate in real time a change in the average flow rate, which may trigger the pacing device 48 to update the lower rate automatically. Alternatively, the pacing device 48 may be programmed remotely by a clinician based on the updated average flow rate data.

In another configuration, the pacing device 48 may update the lower rate by measuring impedance across the right ventricle in a patient having the pump 10. For example, the leads of the pacing device 48 may be configured and positioned to measure impedance across the right ventricle. A change in impedance can be directly correlated to a change in volume, which can be correlated to a change in the target heart rate by the above equation. As the volume increases in the right ventricle, the impedance decreases. Thus, if the impedance changes the target heart rate may change, and similarly, the lower rate, to be correlated with any change in impedance. In such a configuration, the pacing device 48 indirectly communicates with the pump 10 may correlated changes impedance in the right ventricle as a result of the pump 10 to a lower rate for pacing.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of operating a blood pump and a pacing device, the method comprising:
    determining an end diastolic volume (EDV) and an ejection fraction of a ventricle of a heart of a patient at a pump set speed of the blood pump;
    determining an average flow rate based on the pump set speed;
    determining a lower rate for the pacing device based at least in part on the EDV, the ejection fraction, and the average flow rate, the pacing device being in electrical communication with a chamber of the heart; and
    pacing the chamber of the heart when a measured heart rate drops below the lower rate.

2. The method of claim 1, further including measuring a flow rate from the blood pump and updating the lower rate based at least in part on the measured flow rate.

3. The method of claim 1, wherein the blood pump is a left ventricular assist device (LVAD), and wherein the EDV and the ejection fraction are determined from a right ventricle of the heart.

4. The method of claim 1, wherein the blood pump is a right ventricular assist device (RVAD), and wherein the EDV and the ejection fraction are determined from a left ventricle of the heart.

5. A cardiac rhythm and blood flow management system, comprising:
- a blood pump configured to operate at a pump set speed; and
- a pacing device in communication with the blood pump, wherein the pacing device is configured to deliver therapy to a heart of a patient; and
- processing circuitry configured to:
  - determine a flow rate based on the pump set speed, and
  - determine a lower rate for the pacing device based at least in part on the flow rate, wherein the pacing device is configured to deliver the therapy to the heart when a measured heart rate of the patient drops below the lower rate.

6. The system of claim 5, wherein the pacing device is configured to deliver the therapy to a right ventricle or a left ventricle of the heart.

7. The system of claim 5, wherein the flow rate is an average flow rate.

8. The system of claim 5, wherein to determine the flow rate, the processing circuitry is configured to measure the flow rate.

9. The system of claim 5, wherein the processing circuitry is further configured to:
- determine an end diastolic volume (EDV) and an ejection fraction of a chamber of the heart at the pump set speed, and
- determine the lower rate based at least in part on the EDV, the ejection fraction, and the flow rate.

10. The system of claim 5, wherein the blood pump and the pacing device are configured to communicate through a wired connection.

11. The system of claim 5, wherein the blood pump and the pacing device are configured to wirelessly communicate.

12. The system of claim 5, wherein the blood pump is sensorless.

13. The system of claim 5, wherein the pacing device is configured to:
- measure impedance across a ventricle of the heart, and
- update the lower rate based at least in part on the measured impedance.

14. A system comprising:
- a pacing device configured to deliver therapy to a heart of a patient; and
- processing circuitry configured to:
  - determine an end diastolic volume (EDV) and an ejection fraction of a ventricle of the heart at a pump set speed of a blood pump of the patient,
  - determine an average flow rate of blood exiting the blood pump, and
  - determine a lower rate for the pacing device based at least in part on the EDV, the ejection fraction, and the average flow rate.

15. The system of claim 14, wherein the pacing device is configured to deliver the therapy to the heart when a measured heart rate of the patient drops below the lower rate.

16. The system of claim 14, further comprising the blood pump.

17. The system of claim 16, wherein the blood pump is an implantable sensorless blood pump.

18. The system of claim 14, wherein the pacing device is configured to:
- measure impedance across the ventricle, and
- update the lower rate based at least in part on the measured impedance.

19. The system of claim 14, wherein the processing circuitry is configured to determine the average flow rate by at least measuring flow from the blood pump.

* * * * *